United States Patent
McMaster et al.

(10) Patent No.: US 9,091,626 B2
(45) Date of Patent: Jul. 28, 2015

(54) SEALLESS RHEOMETER DIE ASSEMBLY

(71) Applicant: Alpha Technologies Services LLC, Akron, OH (US)

(72) Inventors: Matthew S. McMaster, Wadsworth, OH (US); Henry Pawlowski, Seville, OH (US); Michael R. Stoller, Orrville, OH (US)

(73) Assignee: Alpha Technologies Services LLC, Akron, OH (US)

( * ) Notice: Subject to any disclaimer, the term of this patent is extended or adjusted under 35 U.S.C. 154(b) by 334 days.

(21) Appl. No.: 13/828,201

(22) Filed: Mar. 14, 2013

(65) Prior Publication Data

US 2014/0260558 A1    Sep. 18, 2014

(51) Int. Cl.
*G01N 11/16* (2006.01)
*G01N 33/44* (2006.01)

(52) U.S. Cl.
CPC .............. *G01N 11/165* (2013.01); *G01N 33/44* (2013.01)

(58) Field of Classification Search
CPC ....... G01N 3/24; G01N 11/00; G01N 11/142; G01N 11/16; G01N 11/162; G01N 11/165; G01N 11/167; G01N 33/44; G01N 33/445; G01N 2203/0007; G01N 2203/0025; G01N 2203/0092; G01N 2203/0226; G01N 2203/0694; G01N 2203/0094
See application file for complete search history.

(56) References Cited

U.S. PATENT DOCUMENTS

| | | | | |
|---|---|---|---|---|
| 4,337,646 A | * | 7/1982 | Fraleigh | 73/54.24 |
| 4,421,424 A | * | 12/1983 | Price et al. | 374/48 |
| 4,552,025 A | * | 11/1985 | Barker et al. | 73/846 |
| 4,584,882 A | * | 4/1986 | Tosaki | 73/847 |
| 5,079,956 A | * | 1/1992 | Burhin et al. | 73/846 |
| 5,311,767 A | | 5/1994 | Mathews et al. | |
| 6,164,818 A | | 12/2000 | Dick et al. | |
| 6,336,357 B1 | | 1/2002 | Pawlowski et al. | |
| 6,523,397 B1 | * | 2/2003 | Tosaki | 73/54.39 |
| 7,475,592 B2 | | 1/2009 | Grow et al. | |
| 2007/0220990 A1 | | 9/2007 | Putman et al. | |

FOREIGN PATENT DOCUMENTS

EP    0 511 190 A1    10/1992
WO   WO 01/22053 A1   3/2001

OTHER PUBLICATIONS

International Search Report and Written Opinion for International Application No. PCT/US2014/024225 mailed Jul. 7, 2014.

* cited by examiner

*Primary Examiner* — David A Rogers
(74) *Attorney, Agent, or Firm* — Wolf, Greenfield & Sacks, P.C.

(57) ABSTRACT

A sealless die assembly with a backing element is disclosed. A first die assembly cooperates with a second die assembly to form a sample-holding chamber. At least one of the die assemblies includes a die and a housing that are separated from one another by a radial gap such that the die is rotatable relative to its housing. A thin film is positioned to bridge the gap between the die and its housing to maintain pressure in the sample-holding chamber. A backing element cooperates with the die housing to interface with the film, and the backing element is spaced from its corresponding die. The backing element helps to transfer torque from the sample to the torque transducer. The die assembly may be incorporated into a rheometer or other sampling measuring apparatus for testing process characteristics of a material.

20 Claims, 3 Drawing Sheets

SEALLESS RHEOMETER DIE ASSEMBLY

FIELD

Aspects relate generally to a sealless rheometer die assembly with a backing element and film.

DISCUSSION OF RELATED ART

Various types of rheometers exist to test the process characteristics of materials, such as rubber, vulcanized rubbers, polymers, plastics, thermoplastics, and other materials. In a typical rheometer, a material sample is placed within a chamber defined between two rheometer dies. A rotational strain is applied to the sample on one side of the sample and a measuring device is provided on the other side to measure the torque on the sample. For example, one rheometer die may oscillate relative to a stationary rheometer die to create a rotary shear force on the sample. A torque transducer may be mounted on the stationary die to measure the torque on the sample which indicates the response of the sample to the shear force.

SUMMARY

The inventor has found that conventional rheometers with pressurized sample cavities require frequent recalibration and seal replacement, which can be inefficient and costly. The inventor has recognized that these issues originate in the sealing arrangement of the die assembly on the side where the torque transducer is located. In conventional die assemblies, an elastomeric seal is held by the die housing and is in contact with both the die and the die housing. The seal will deform during use because the torque transducer must be allowed to deform in order to make a measurement. Elastic properties of the seal may change with time due to exposure to high temperatures and wear from frictional forces. As the seal ages and wears the instrument must be recalibrated, and eventually, the seal must be replaced altogether.

The inventor has appreciated that such need for recalibration and seal replacement may be reduced by replacing the conventional seal with a film and backing element configuration. The film keeps the sample-holding chamber pressurized, and the backing element, which is disposed against the die housing and positioned between the die housing and the film in the area, reduces drag between the film and the die housing. Unlike the conventional seal, the backing element is spaced from the die such that the backing element does not contact the die. Accordingly, with the backing element spaced from the die, minor changes to the backing element shape or properties and wear of the backing element do not affect the measurement of the torque on the sample.

According to one aspect, a rheometer for measuring properties of a sample material includes a first die assembly with a first die and a first sealing plate. A gap is located between the first die and the first sealing plate. The rheometer also includes a second die assembly with a second die and a second sealing plate. The first and second dies form a sample-holding chamber. The rheometer also includes a backing element that cooperates with the first sealing plate, where a portion of the backing element interfaces with the sample-holding chamber. The first and second die assemblies are arranged to accept a film to be positioned between the first and second dies such that the film bridges the gap between the first die and the first sealing plate. When the film is held between the dies, the backing element is spaced from the first die with the film separating the backing element from the sample-holding chamber.

According to another aspect, a method for measuring properties of a sample material using a rheometer is disclosed. The rheometer includes a first die assembly with a first die and a first sealing plate, a backing element that cooperates with the first sealing plate, and a second die assembly with a second die and a second sealing plate. The first and second dies form a sample-holding chamber. The method includes placing a sample in the sample-holding chamber. The method also includes placing a film between the sample and the first die assembly to bridge a gap between the first die and the first sealing plate such that, when the first and second die assemblies are in the closed position, the backing element is spaced from the first die, and the film separates the backing element from the sample-holding chamber.

According to yet another aspect, a rheometer for measuring properties of a sample material includes a first die assembly with a first die and a first sealing plate. A gap is located between the first die and the first sealing plate. The rheometer also includes a second die assembly with a second die and a second sealing plate. The first and second dies form a sample-holding chamber. The rheometer also includes a backing element that cooperates with the first sealing plate. Finally, the rheometer includes a film positioned between the first and second dies such that the film bridges the gap between the first die and the first sealing plate. When the first and second die assemblies are in the closed position, the backing element is spaced from the first die, and the film separates the backing element from the sample-holding chamber.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. Various embodiments of the invention will now be described, by way of example, with reference to the accompanying drawings, in which.

DETAILED DESCRIPTION

Rheometers are typically used to determine various properties of a viscoelastic material, such as rubber, vulcanizable rubbers, polymers, plastics, thermoplastics, or other material. These instruments may be commonly referred to as Moving Die Rheometers (MDR), Rubber Process Analyzers (RPA), Oscillating Disk Rheometers (ODR) and/or Mooney Viscometers. These instruments may apply a rotational shear force to a material sample and may measure the resulting torque on the sample. Information about the material may be derived from the measured torque on the sample. The material sample to be tested may be enclosed within a chamber formed between two opposing rheometer dies and the rotational shear force may be applied to the material sample by rotating one die while the other die remains stationary. It should be appreciated that the term "rheometer" refers to any rheological instrument used to measure a process characteristic of a viscoelastic material, including, but not limited to, the devices listed above.

As discussed above, a rheometer may be configured with dies forming the upper and lower portions of the sample-holding chamber. In a conventional rheometer, each die is a circular disc rotatable in a co-axial cylindrical housing surrounding the die. An annular seal of a heat-resistant elastomeric material is seated in a groove in an axially-extending face of the die housing and in contact with an axially-extending face of the die. Such seals have been required to maintain a constant pressure in the sample-holding chamber during the test. However, the seal is subjected to constant wear due to contact with the die during relative movement between the housing and the die. In addition, contact between the sample and the seal can also increase the wear on the seal. As a result, such seals can wear out quickly, requiring frequent recalibration of the instrument and replacement of the seal.

Figure 1:
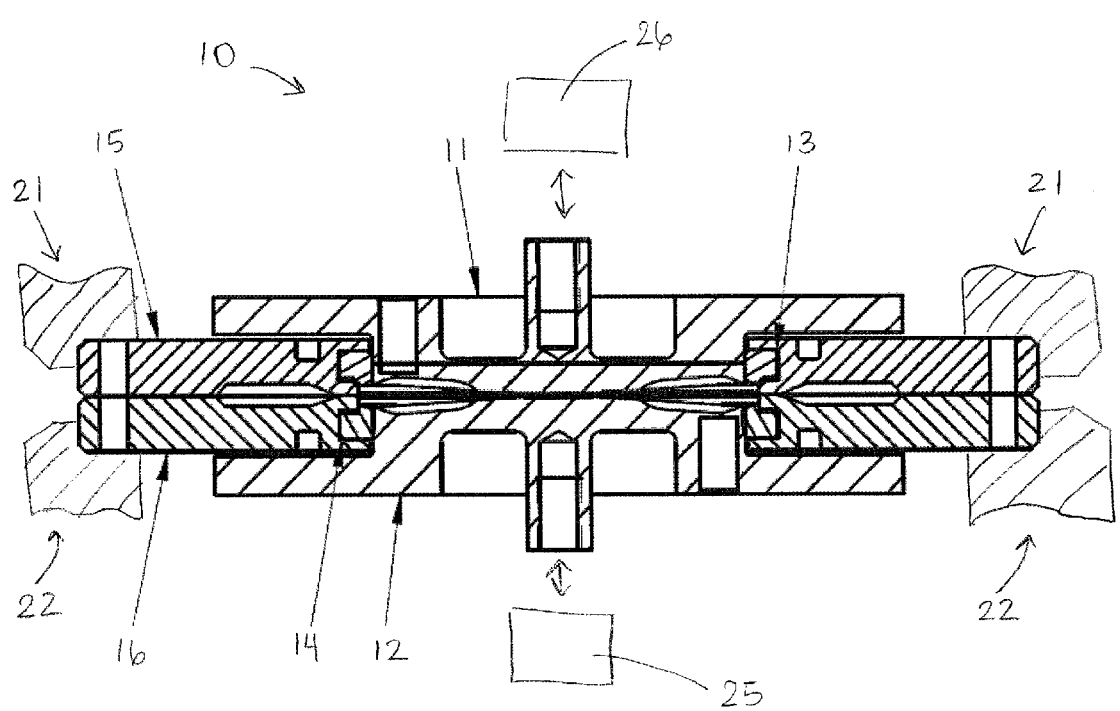
FIG. 1 is a cross-sectional view of a portion of a conventional rheometer.

For example, FIG. 1 illustrates an exemplary conventional rheometer 10. An upper die assembly comprises upper housing 21 and upper die 11. Upper housing 21, which includes upper sealing plate 15, surrounds upper die 11. Upper seal 13 is seated in a groove in the axially-extending face of upper sealing plate 15 and is in contact with upper die 11 at an inner annular face of the seal. A lower die assembly comprises lower housing 22 and lower die 12 also at an inner annular surface of the seal. Housing 22, which includes lower sealing plate 16, surrounds lower die 12. Lower seal 14 is seated in a groove in the axially-extending face of lower sealing plate 16 and is in contact with lower die 12. Upper die 11 connects to a torque transducer 26 via fasteners around the periphery of upper die 11. Lower die 12 connects to a drive mechanism 25 via fasteners around the periphery of lower die 12. Upper seal 13, which is seated in upper sealing plate 15 and around the upper die 11, imparts a drag on the movement of the upper die 11. The amount of drag changes when the physical properties of the seal change due to extreme temperatures and substantial wear due to contact with the sample present in the chamber. Such changes in drag may distort torque measurements at the torque transducer and lead to inaccurate results.

There have been several attempts to avoid such a seal arrangement. For example, according to one approach, the seal between the die and die housing is removed and the sample-holding chamber is left open to atmospheric pressure. The inventors have appreciated that, in such an arrangement, the sample-holding chamber is no longer pressurized, allowing air bubbles to form within the sample, thereby giving rise to measurement distortion and inaccurate results.

According to another approach, the elastomeric seal between the die and die housing is removed and a film is placed between the sample and the die to bridge a gap between the die and the die housing. The inventors have appreciated that, in such an arrangement, the film adheres to the die housing and the upper die and gives rise to a significant drag force between the die and the die housing via the film that creates measurement distortion and inaccurate results. Stiffer test materials also contribute to measurement distortion by creating an additional drag force between the upper die and the die housing.

According to another approach, the heat-resistant elastomeric seal is replaced with a bearing material. The inventors have appreciated that, because bearing materials cannot handle temperature changes well, the use of bearing materials in a rheometer die assembly may cause gap size changes between the die and the die housing due to fluctuations in temperature during the testing process, resulting in issues with repeatability. In addition, the inventors have appreciated that it is difficult to manufacture such a device in a repeatable way in multiple rheometers.

Aspects of the invention are directed to a die assembly which is configured to produce accurate and repeatable measurement while reducing the frequency of instrument recalibration and seal replacement. Also, this arrangement allows multiple rheometers to operate in a more repeatable manner.

According to an aspect, the conventional elastomeric seal that contacts both the die and the die housing is eliminated while the pressure in the sample-holding chamber is maintained with a configuration that reduces or eliminates drag.

In one embodiment, a die assembly includes a film and a backing element. The film bridges a gap between a die and its housing to maintain pressure in the sample-holding chamber while the presence of the backing element reduces or eliminates drag between the film and the die housing. In this manner, frequent instrument recalibration due to seal wearing is reduced due to the absence of the conventional seal, while the film maintains pressure in the sample-holding chamber. Maintaining pressure in the test chamber may be desirable for a variety of reasons, including reducing the likelihood of formation of air bubbles in the sample, as will be explained.

Figure 2:
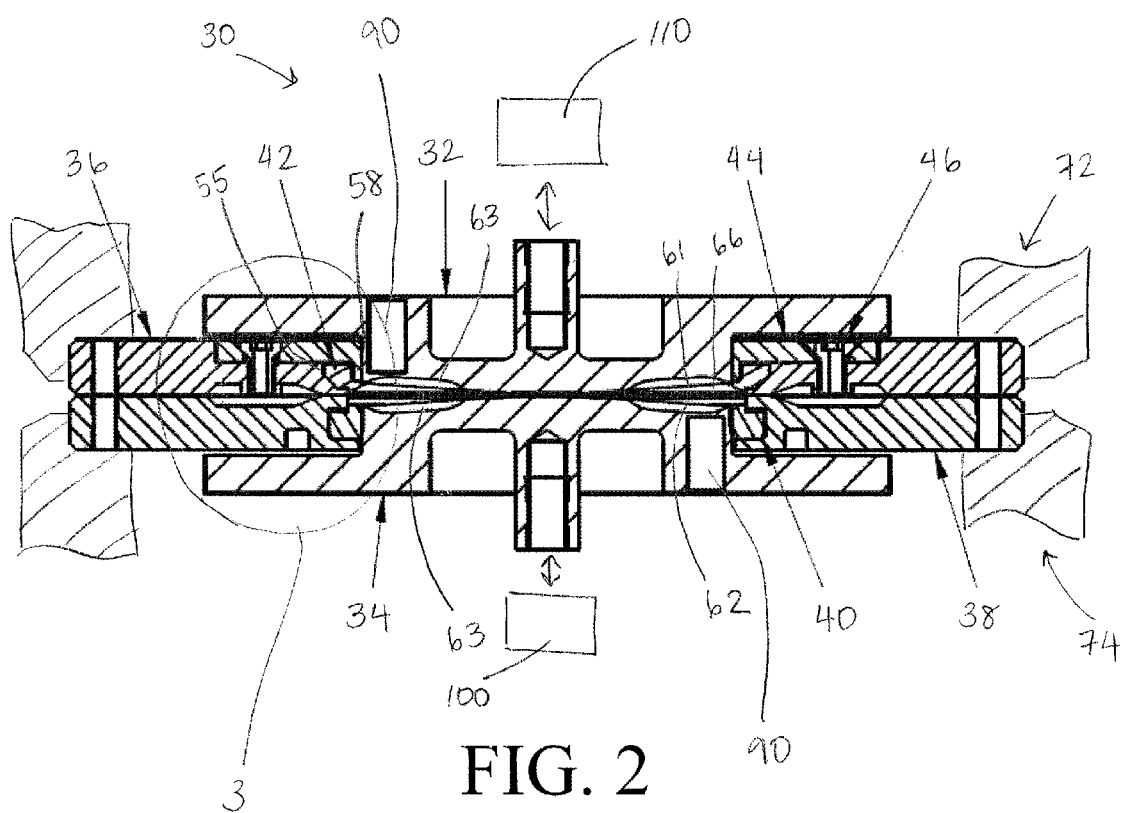
FIG. 2 is a cross-sectional view of an exemplary rheometer according to one illustrative embodiment.

As shown in FIG. 2, rheometer 30 includes an upper die assembly which comprises upper housing 72 and upper die 32. Upper housing 72, which includes an upper sealing plate 36, surrounds upper die 32. A lower die assembly comprises lower housing 74 and lower die 34. Lower housing 74, which includes a lower sealing plate 38, surrounds lower die 34. Opposing faces 61, 62 of dies 32, 34 are axially movable relative to one another between an open position and a closed position. An annular seal 40 is seated in a groove in the axially-extending face of lower sealing plate 38 and is in contact with lower die 34.

Figure 3:
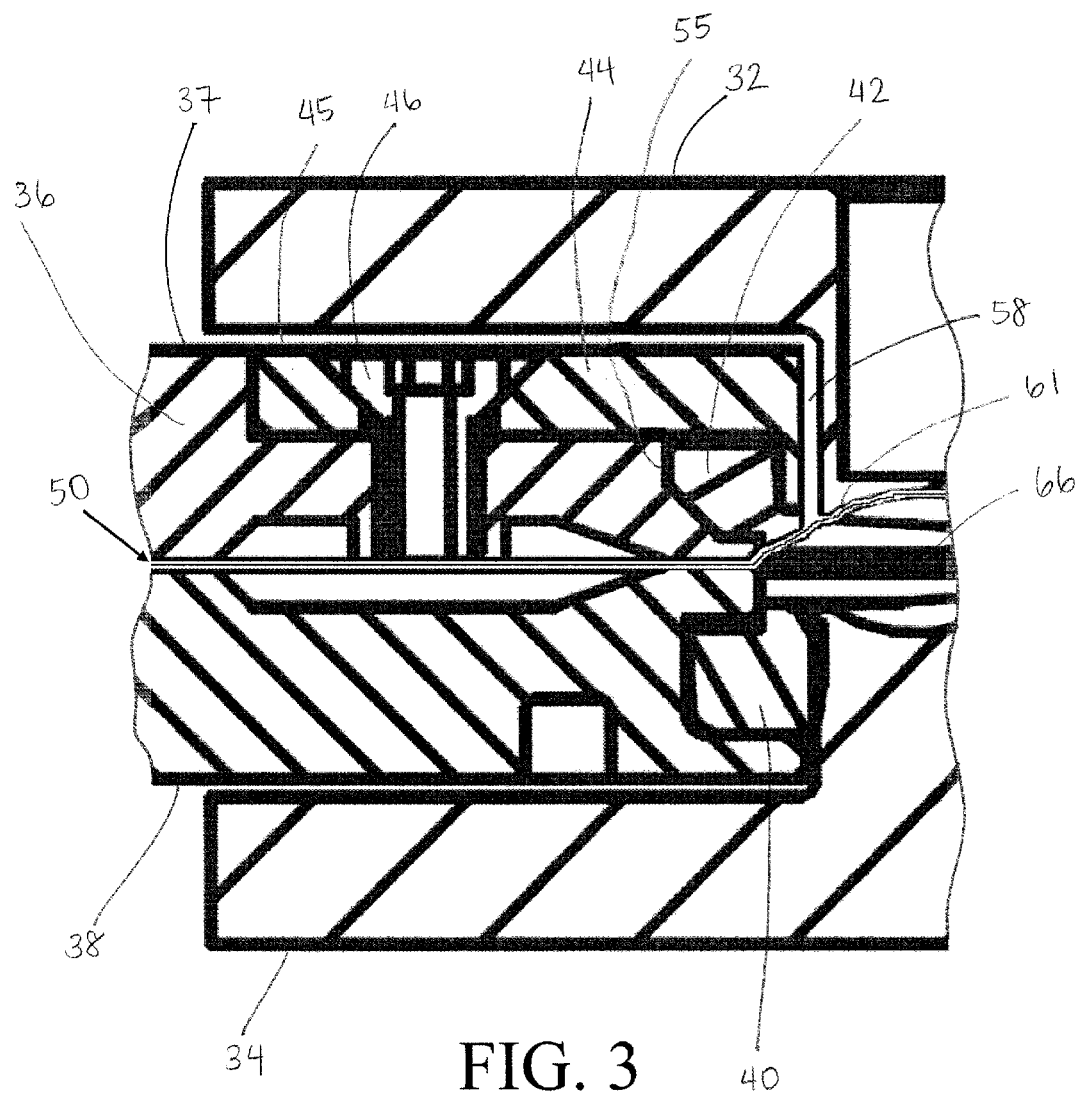
FIG. 3 is an enlarged view of a portion of the rheometer of FIG. 2 encircled by line 3.

As seen most clearly in FIG. 3, a small, substantially circumferential gap 58 separates upper sealing plate 36 from upper die 32. Accordingly, forces applied to upper die 32 are not transferred to the upper sealing plate 36. This allows a torque transducer 110 to accurately measure the torque applied to upper die 32 by the sample located between the upper and lower die 34 as the lower die 34 rotates. In some embodiments, gap 58 may be between 0.005 to 0.008 inches. Any suitable gap size that does not cause leakage may be used, as this aspect is not limited in this regard. Alternatively or in addition, the gap 58 may also separate the upper die 32 from the retaining ring 44 and/or the backing element 42.

A film 50 is positioned between the upper and lower die assemblies to bridge this gap 58 between the upper sealing plate 36 and the upper die 32. The presence of film 50 serves to seal sample-holding chamber 66 from atmospheric pressure, allowing sample-holding chamber 66 to remain pressurized during testing. Maintaining a pressurized sample-holding chamber 66 helps to prevent formation of air bubbles that distort measurements.

Various polymer films having non-adhesive and thermal characteristics may be used for film 50, for example aromatic polyesters, polyamides and polyimides. Certain mixed polyimide/polyamide or polyester ether ketone films can also be used, for example, 'Kapton' polyimide film. In addition, metallized polymer films may also be used, as well as certain metallic films or foils. In some embodiments, CHANGSHU HUACHIANG CH250 may be used. In some embodiments, DUPONT KAPTON 100 HN may be used.

In some embodiments, the film may have a tensile strength at break in the range 175-215 MPa in the machine direction and 225-275 MPa in the transverse direction, a yield stress in the range 85-105 MPa in both directions, and an elongation at break in the range 110-140% in the machine direction and 70-90% in the transverse direction. These values are determined by ASTM method D-882-83 carried out at 23 degrees Celsius, 50% relative humidity and a strain rate of 50% per min. In some embodiments, the film may have a tensile strength at break of 139 MPa in the machine direction and 120 MPa in the transverse direction, a yield stress of 69 MPa, and an elongation at break of 40%.

Films of various thickness can be used. In some embodiments, the film has a thickness in the range of 15-50 micrometers. In some embodiments, the film has a thickness in the range of 20-25 micrometers. In some embodiments, the film has a thickness in the range of 15-100 micrometers. In some embodiments, the film has a thickness of 25 micrometers.

The film may be sandwiched between the upper and lower die assemblies. In some cases, the film may be replaced after each test. In some embodiments, a first film is used to separate the sample from the upper die assembly, and a second film is used to separate the sample from the lower die assembly. In other embodiments, film is used to separate the sample from the upper die assembly, while film is not used to separate the sample from the lower die assembly.

When a film is used to keep the sample-holding chamber pressurized, contact between the film and the die housing during testing creates drag that distorts measurements and leads to inaccurate results. In one embodiment, this drag between the film and the die housing is reduced by the presence of a backing element between the film and the die housing. To prevent contact between the film and the housing, a backing element cooperates with the housing such that the film interfaces with the backing element instead of with the housing.

In one embodiment, as seen in FIG. 2, backing element 42 is an annular member that cooperates with upper housing 72 and is seated in a groove in upper sealing plate 36. The upper sealing plate 36 forms part of upper housing 72.

As best seen in FIG. 3, backing element 42 cooperates with upper sealing plate 36 of the upper die housing 72. When the upper and lower dies 32, 34 are in the closed position to form the sample-holding chamber 66, backing element 42 is positioned such that, with the film 50 removed, the portion of the backing element 42 closest to the sample-holding chamber 66 interfaces with the sample-holding chamber 66.

With the film 50 positioned between the upper and lower dies 32, 34, the backing element 42 is positioned between film 50 and the upper sealing plate 36 of the upper die housing 72 in the area surrounding opposing face 61 of upper die 32. Due to the presence of backing element 42, contact between film 50 and upper sealing plate 36 in the area surrounding opposing face 61 of upper die 32 is reduced, and in some embodiments, eliminated, thereby reducing creation of drag forces between film 50 and upper sealing plate 36. Instead, film 50 contacts backing element 42 when the film 50 moves relative to the backing element 42 during testing. In some embodiments, the backing element 42 may be situated to allow the film 50 to only come in contact with the backing element 42 in the area surrounding the opposing face 61 of upper die 32.

The backing element 42 is spaced from the upper die to avoid wear of the backing element. In one embodiment, as best seen in FIG. 3, backing element 42 is spaced from upper die 32 by gap 58. During rotation of upper die 32 relative to upper sealing plate 36, backing element 42 does not contact upper die 32. Due to its isolation from upper die 32, backing element 42 is not subject to the frictional forces that may wear away conventional rheometer seals. Furthermore, film 50 separates the backing element 42 from the sample-holding chamber 66 such that sample does not contact the backing element 42 during the testing process.

Backing element 42 may cooperate with upper sealing plate 36 in any suitable arrangement. In some embodiments, backing element 42 may remain disposed against upper sealing plate 36 due to an interference fit of backing element 42 within a circumferential groove 55 in the upper sealing plate 36. Alternatively or in addition, other suitable retaining arrangements may be used to maintain contact between the backing element 42 with the upper sealing plate 36. In some embodiments, a retainer helps to maintain contact between the backing element and the housing. The retainer exerts a retaining force upon the backing element to prevent movement of the backing element relative to the die housing. In the embodiment shown in FIG. 2, retaining ring 44 cooperates with the upper die housing 72 to exert a retaining force upon backing element 42 by compressing backing element 42 between retaining ring 44 and upper sealing plate 36. As shown in FIGS. 2-3, a portion of backing element 42 is located between retaining ring 44 and upper sealing plate 36.

The retaining ring 44 may be secured to upper sealing plate 36 in any suitable way. A fastener 46 may be used to attach retaining ring 44 to the upper sealing plate 36. Any suitable fastener may be used to attach retaining ring 44 to the upper sealing plate 36, such as a screw or other suitable hardware. In some embodiments, retaining ring 44 may attach to upper sealing plate 36 without the use of fasteners, for example, via an interference fit, a dovetail joint, or other suitable arrangements.

In some embodiments, to achieve a compact and/or streamlined configuration, retaining ring 44 may cooperate with the upper sealing plate 36 to form a single unitary body or shape. Retaining ring 44 may cooperate with the upper sealing plate 36 such that the surface 45 of the retaining ring 44 is flush with the surface 37 of the upper sealing plate 36, and thus retaining ring 44 and upper sealing plate 36 combine to form a single unitary shape. In some embodiments, the upper sealing plate may be integrally formed with a retainer such that the upper sealing plate and retainer form a single component.

Of course, it should be appreciated that a backing element 42 may cooperate with upper sealing plate 36 to maintain contact with the upper sealing plate 36 or to be otherwise disposed against upper sealing plate 36 by any suitable means, as this aspect is not limited in this regard. For example, the backing element 42 may be held by upper sealing plate 36 by an interference fit alone. As another example, the backing element 42 may be directly attached to upper sealing plate 36 by fasteners. Alternatively or in addition, backing element 42 may be simply seated within a recess or groove in upper sealing plate 36 and remain disposed against upper sealing plate 36 without an interference fit. In still other embodiments, the backing element may be adhered in place.

FIGS. 2 and 3 depict a single backing element, film and retainer arrangement only at the die that is coupled to the torque transducer. Alternatively or in addition, the same or similar backing element, film and retainer arrangement may be used at the die that is coupled to the drive mechanism. For example, in one embodiment, the annular seal 40 at lower die 34 shown in FIGS. 2-3 is replaced by a backing ring, film and retainer arrangement similar to that used at upper die 32.

The material of backing element 42 may be chosen such that it may flex along with the material in the sample chamber. The backing element may be made from any suitable elastomer.

The material of backing element 42 may also be chosen such that sliding contact between film 50 and backing element 42 creates less drag force than sliding contact between film 50 and upper sealing plate 36. The backing element is made of a material of sufficient lubricity to avoid adherence between it and the film. For example, the backing element may be made of polytetrafluoroethylene (PTFE), or any suitable elastomer, such as a fluoroelastomer. In addition, the backing element may be made of other materials that can reduce drag such as graphite or bearing type materials.

Additional features of an exemplary rheometer are now discussed. The upper die assembly and lower die assembly are axially movable relative to one another between an open position and a closed position. To achieve the closed position shown in FIG. 2, the upper and lower die assemblies are moved toward one another such that the opposing faces 61 and 62 of dies 32, 34 define a sample-holding chamber 66 for holding a material sample. The sample-holding chamber 66 may have a predetermined shape and volume. When the upper and lower die assemblies are moved away from one another into the open position, the sample can be inserted or removed from between the upper and lower dies 32, 34. According to another embodiment, the sample may be injected into the rheometer.

As seen in FIG. 2, the opposing faces 61 and 62 of dies 32, 34 are in the form of shallow flat-topped cones (i.e., bioconical plates) having radial grooves 63. Thus, a sample in the sample-holding chamber 66 has a thin, flat circular portion in the middle, and an outer portion which increases in thickness radially outwards. It should be appreciated that opposing faces 61 and 62 may have other configurations, including a generally planar surface (i.e., parallel plates). The biconical plate configuration is typically used for rubber materials, while the flat plate configuration is typically used for either rubber, plastic materials or resin impregnated fiber.

To impart a shear force onto a sample held in sample-holding chamber, one die may move relative to the other die. In the illustrative embodiment of FIG. 2, the upper die 32 is stationary, while the lower die 34 is coupled to a drive mechanism 100 for rotation. It should be appreciated that in other embodiments, the upper die 32 may be configured for movement while the lower die 34 may be stationary, as the present invention is not limited in this respect. A drive mechanism 100 is coupled to the lower die 34 in known fashion to impart movement of the lower die 34. It should be appreciated that various components may be used to generate die movement, as the present invention is not so limited. The applied rotational shear force created by the moving die 34 may be oscillatory or continuous and may have a predetermined amplitude and frequency. According to one embodiment, the applied shear force is at an amplitude of oscillation within a range of approximately +/−0.1° arc to +/−180° arc, with a frequency of oscillation within a range of approximately 0.001 Hz to 50 Hz. However, it should be appreciated that the present invention is not limited to the application of a particular type of shear force on the material sample. It is contemplated that other amplitude and frequency ranges may be utilized, as the present invention is not so limited. In one embodiment, the lower die may rotate continuously in one direction. In another embodiment, a stress relaxation test may be used, in which the lower die undergoes a brief rapid movement in one direction and then stops. To measure the torque on the sample held in sample-holding chamber, the rheometer is coupled to a torque transducer. In the illustrative embodiment of FIG. 2, a torque transducer 110 is coupled to the stationary upper die 32 in known fashion. In another embodiment, the torque transducer 110 may be coupled to other suitable components and/or at other suitable locations that will experience a measurable strain or torque, as the present aspect is not so limited. It should be appreciated that various types of torque transducers or other suitable devices and/or arrangements may be used to measure the torque on the sample, as the present aspect is not limited in this respect.

The measured resulting torque on the sample may be an indication of the particular response of the sample material to the particular applied shear force. Process characteristics of the sample material may be derived from the measured torque. For example, the elastic torque, viscous or loss torque and the modulus of the sample material may be determined based upon calculations with the measured complex torque on the sample, the frequency and amplitude of the rotation, and the dimensions of the dies. Any suitable methodology may be employed, and thus are not described in detail in the present application.

Process characteristics of a material may change significantly by varying temperature, frequency and/or strain. Testing at several different frequencies, strains and temperatures may be necessary to adequately characterize a material sample. In one embodiment, the desired frequency, strain, and temperature for a particular test may be programmed into a computer which interfaces with the rheometer.

In some test arrangements, the material sample may be heated so that the sample conforms to the rheometer dies. The sample may also be heated to test various process characteristics of the material at certain temperatures. Heaters and temperature sensors may be provided to control the temperature of the sample. In general, the softer the material, the lower the torque on the sample. However, as a sample cools from a molten or semi-molten state to a more solid state, the harder samples increases the measured torque. As illustrated in FIG. 2, temperature sensors 90 may be provided on one or more dies to measure and assist in controlling the temperature of the sample. A sensor may be positioned closer to the surface of the die which contacts the sample to more accurately measure the temperature of the sample.

Other features of a conventional rheometer may be used in connection with the rheometer and sealless rheometer die assembly discussed herein. Such additional features will be readily apparent to one of skill in the art.

It should be appreciated that the invention is not limited in this regard as one or any combination of these listed purposes may be obtained and that the invention is not limited to a die assembly that achieves all of them. In addition, the invention is not limited to achieving any of these purposes. Instead, as stated, a desired outcome is obtaining more accurate measurements with less instrument recalibration and seal replacement than what was available in the past.

It should be appreciated that the die assembly described here may be formed with one or more of the above-described features. The above aspects and features may be employed in any suitable combination as the present invention is not limited in this respect. It should also be appreciated that the drawings illustrate various components and features which may be incorporated into various embodiments of the invention. For simplification, some of the drawings may illustrate more than one optional feature or component. However, the invention is not limited to the specific embodiments disclosed in the drawings. It should be recognized that some embodiments may include only a portion of the components illustrated in any one drawing figure, and/or may also encompass embodiments combining components illustrated in multiple different drawing figures.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. A rheometer for measuring properties of a sample material, comprising:
   a first die assembly comprising a first die and a first sealing plate;
   a gap between the first die and the first sealing plate;
   a second die assembly comprising a second die and a second sealing plate, the first and second dies forming a sample-holding chamber; and
   a backing element cooperating with the first sealing plate, wherein a portion of the backing element interfaces with the sample-holding chamber,
   wherein:
   the first and second die assemblies are arranged to accept a film to be positioned between the first and second dies to bridge the gap between the first die and the first sealing plate, and when the film is held between the dies, the backing element is spaced from the first die with the film separating the backing element from the sample-holding chamber.

2. The rheometer of claim 1, further comprising a retainer cooperating with the first sealing plate to prevent movement of the backing element relative to the first sealing plate.

3. The rheometer of claim 2, wherein at least a portion of the backing element is positioned between the retainer and the first sealing plate.

4. The rheometer of claim 2, wherein a portion of the retainer is positioned between the backing element and the first die.

5. The rheometer of claim 1, further comprising a drive mechanism coupled to the second die, the drive mechanism constructed and arranged to rotate one of the first or second dies relative to the other die.

6. The rheometer of claim 1, further comprising a seal positioned between the second die and the second sealing plate.

7. The rheometer of claim 1, wherein at least a portion of the backing element comprises polytetrafluoroethylene.

8. The rheometer of claim 1, wherein at least a portion of the backing element comprises an elastomer.

9. The rheometer of claim 1, wherein the elastomer comprises a fluoroelastomer.

10. The rheometer of claim 1, wherein the backing element comprises a low friction material.

11. The rheometer of claim 10, wherein the backing element comprises graphite.

12. The rheometer of claim 10, wherein the backing element comprises a lubricant.

13. The rheometer of claim 1, wherein the first and second die assemblies have an open and a closed position.

14. The rheometer of claim 1, wherein at least one of the first and second dies is rotatable relative to the other of the first and second dies.

15. The rheometer of claim 1, further comprising a torque transducer coupled to the first die constructed and arranged to measure the torque on a sample in the sample-holding chamber.

16. The rheometer of claim 1, wherein the film comprises a polyimide material.

17. The rheometer of claim 1, wherein the film has a thickness between 15 micrometers to 50 micrometers.

18. The rheometer of claim 1, further comprising:
   a second backing element cooperating with the second sealing plate; and
   a second gap between the second die and the second sealing plate;
   a second film positioned between the first and second dies to bridge the second gap between the second die and the second sealing plate,
   wherein, when the first and second die assemblies are in the closed position, the second backing element is spaced from the second die, and the second film separates the second backing element from the sample-holding chamber.

19. A method for measuring properties of a sample material using a rheometer comprising a first die assembly comprising a first die and a first sealing plate, a backing element that cooperates with the first sealing plate, and a second die assembly comprising a second die and a second sealing plate, the first and second dies forming a sample-holding chamber, wherein the method comprises:
   placing a sample in the sample-holding chamber;
   placing a film between the sample and the first die assembly to bridge a gap between the first die and the first sealing plate such that, when the first and second die assemblies are in the closed position, the backing element is spaced from the first die, and the film separates the backing element from the sample-holding chamber.

20. A rheometer for measuring properties of a sample material, comprising:
   a first die assembly comprising a first die and a first sealing plate;
   a gap between the first die and the first sealing plate;
   a second die assembly comprising a second die and a second sealing plate, the first and second dies forming a sample-holding chamber; and
   a backing element cooperating with the first sealing plate; and
   a film positioned between the first and second dies to bridge the gap between the first die and the first sealing plate,
   wherein, when the first and second die assemblies are in the closed position, the backing element is spaced from the first die, and the film separates the backing element from the sample-holding chamber.

* * * * *